(12) United States Patent  
Glisan et al.

(10) Patent No.: US 11,877,919 B2  
(45) Date of Patent: Jan. 23, 2024

(54) MALE INCONTINENCE CONTROL DEVICE AND METHOD OF CONTROLLING MALE INCONTINENCE

(71) Applicant: ASSURE MEDICAL GROUP, LLC, Minneapolis, MN (US)

(72) Inventors: Duane L. Glisan, Saint Louis Park, MN (US); Ronald C. Johansson, Stillwater, MN (US)

(73) Assignee: ASSURE MEDICAL GROUP, LLC, Minneapolis, MN (US)

( * ) Notice: Subject to any disclaimer, the term of this patent is extended or adjusted under 35 U.S.C. 154(b) by 873 days.

(21) Appl. No.: 16/755,935

(22) PCT Filed: Nov. 9, 2018

(86) PCT No.: PCT/US2018/060012  
§ 371 (c)(1),  
(2) Date: Apr. 14, 2020

(87) PCT Pub. No.: WO2019/094707  
PCT Pub. Date: May 16, 2019

(65) Prior Publication Data  
US 2020/0297470 A1    Sep. 24, 2020

Related U.S. Application Data

(60) Provisional application No. 62/684,549, filed on Jun. 13, 2018, provisional application No. 62/583,525, filed on Nov. 9, 2017.

(51) Int. Cl.  
*A61F 2/50* (2006.01)  
*A61F 2/00* (2006.01)  
*A61B 18/00* (2006.01)

(52) U.S. Cl.  
CPC .......... *A61F 2/0054* (2013.01); *A61F 2/0004* (2013.01); *A61F 2/0031* (2013.01);  
(Continued)

(58) Field of Classification Search  
CPC .... A61F 2/0054; A61F 2/0031; A61F 2/0004; A61B 2018/00523  
See application file for complete search history.

(56) References Cited

U.S. PATENT DOCUMENTS 4,139,007 A * 2/1979 Diamond .............. A61F 2/0054  
128/842  
4,539,980 A  9/1985 Chaney  
(Continued)

FOREIGN PATENT DOCUMENTS

CA   2824958 A1   1/2014  
CN   102266256 B  5/2013  
(Continued)

OTHER PUBLICATIONS https://web.archive.org/web/20160206131116/https://penileclamps.com/dribblestop-penile-clamp.html.  
https://web.archive.org/web/20160721050548/http://www.vitalitymedical.com/circlamp-male-incontinence-penis-clamp.html.

*Primary Examiner* — Rebecca S Preston  
(74) *Attorney, Agent, or Firm* — SHERRILL LAW OFFICES, PLLC (57) ABSTRACT

A comfortable single-piece male incontinence control device (100) permitting conscious micturition without adjustment or removal of the device (100). The device having a continuous loop of an elastic compression band (110) configured and arranged to securely encircle a flaccid penis P without inflicting penile ischemia, and a bump (120) on the elastic compression band (110) projecting inward into (Continued)

the lumen (119) defined by the band (110) for pressing against and constricting the urethra U of a wearer W.

20 Claims, 5 Drawing Sheets

(52) U.S. Cl.
CPC ............... *A61B 2018/00523* (2013.01); *A61F 2210/0057* (2013.01); *A61F 2230/0008* (2013.01); *A61F 2230/0071* (2013.01); *A61F 2250/001* (2013.01); *A61F 2250/0059* (2013.01); *A61F 2250/0069* (2013.01); *A61F 2250/0078* (2013.01)

(56) References Cited

U.S. PATENT DOCUMENTS

| | | | |
|---|---|---|---|
| 5,306,227 A | 4/1994 | Osbon et al. | |
| 5,842,968 A | 12/1998 | Johnson | |
| 5,855,548 A | 1/1999 | Place | |
| 6,039,750 A | 3/2000 | Kubalak et al. | |
| 6,131,576 A | 10/2000 | Davis | |
| 6,138,678 A * | 10/2000 | Nilsson | A61F 2/0054 128/885 |
| 6,234,174 B1 | 5/2001 | Cheng et al. | |
| 6,289,895 B1 | 9/2001 | Cheng et al. | |
| 6,609,522 B2 | 8/2003 | Cheng et al. | |
| 6,827,085 B2 | 12/2004 | Single et al. | |
| 6,981,505 B2 | 1/2006 | Krause et al. | |
| 7,658,194 B2 | 2/2010 | Anderson et al. | |
| 7,658,195 B2 | 2/2010 | Dennis | |
| 10,624,728 B2 | 4/2020 | Velez Weisner | |
| 2005/0256365 A1 | 11/2005 | Timm et al. | |
| 2006/0081265 A1 | 4/2006 | Warden | |
| 2009/0036729 A1 * | 2/2009 | Anderson | A61F 13/505 600/38 |
| 2013/0053804 A1 | 2/2013 | Sorensen et al. | |
| 2014/0041672 A1 | 2/2014 | Garcia Berruezo | |
| 2019/0060048 A1 * | 2/2019 | Gautieri | A61F 2/0054 |

FOREIGN PATENT DOCUMENTS

| | | | |
|---|---|---|---|
| CN | 204468391 U | 7/2015 | |
| DE | 10213452 C1 | 7/2003 | |
| FR | 2638964 A1 | 5/1990 | |
| GB | 2510391 A * | 8/2014 | ............... A61F 5/41 |
| KR | 101508140 | 4/2015 | |
| WO | 98/44852 | 10/1998 | |
| WO | 99/55251 | 11/1999 | |
| WO | 2014/027344 | 2/2014 | |

\* cited by examiner

MALE INCONTINENCE CONTROL DEVICE AND METHOD OF CONTROLLING MALE INCONTINENCE

BACKGROUND

Male incontinence is a worldwide problem. It can be the byproduct of a wide variety of health issues, including aging, prostate surgery or sphincterotomy, medications, kidney disease, and others. Incontinence can have a major impact on one's lifestyle. The inability to control urination can affect almost every activity, resulting from fear of consequence or embarrassment.

Nursing homes, with an elderly male population, have a great need for a solution to this problem, which also demands staff attention throughout the day. The impact on active younger men with incontinence may be even greater. Early diagnosis of prostate cancer followed by surgery, for example, can lead to many years or decades of daily lifestyle modifications.

Stopping involuntary urinary flow can be achieved by adequately restricting the urethra, but doing so throughout the day while not causing discomfort or inconvenience has proven to be the challenge. Present art is focused on impeding urinary flow while compromising comfort and convenience. Hard-body mechanisms, including clamps and encirclement devices that wrap around the penis circumference, or otherwise, are unyielding and subject to movement when periodic forces are applied when the user is active. Even normal body movement will place periodic asymmetric pressures on such devices, thereby imparting forces which may cause a displacement and/or discomfort. The present art requires removal, adjustment, or repositioning prior to regular urinations. After urination, the process is reversed. Such demands do not always suit the circumstances when the need for urination arises. Convenience is not a medical term, but to many users it can also be a fundamental requirement in addition to comfort, effective urinary control, and limited impact on blood circulation.

Accordingly, a need exists for a male incontinence control device that is convenient to use and performs well without discomfort or required management throughout the day prior to, during, or after urination.

SUMMARY OF THE INVENTION

The invention is directed to a male incontinence control device and related methods of using the device.

In a first embodiment, the male incontinence control device is a male incontinence control device that includes (a) a single-piece continuous loop of an elastic compression band defining a lumen, the elastic compression band configured and arranged to securely encircle a flaccid penis without inflicting penile ischemia, and (b) an inwardly projecting bump on the elastic compression band configured and arranged for pressing against and constricting the urethra of a wearer.

In a second embodiment, the male incontinence control device is (a) a continuous looped band of material defining a lumen wherein the band has an integrated first elastic length and a second inelastic length, and is configured and arranged to securely encircle a flaccid penis without inflicting penile ischemia, and an inwardly projecting bump on the band configured and arranged for pressing against and restricting the urethra of a wearer.

The lumen of the male incontinence control device preferably has an elliptic cross-section with a major axis centered through a top and bottom portion of the elastic compression band and a minor axis centered through side portions of the elastic compression band, and the volumetric center of the bump is essentially aligned with the minor axis.

The device preferably includes diametrically opposed first and second removal loops extending radially outward from the elastic compression band in alignment with the minor axis of the lumen, with the removal loops configured and arranged to accommodate passage of at least one fingertip through each removal loop to facilitate manual outward radial stretching of the elastic compression band.

The device is operable for controlling male incontinence, by (i) manually radially stretching the continuous elastic compression band so as to enlarge the lumen, (ii) inserting the penis of a male in need of incontinence control through the enlarged lumen with the bump on the device positioned proximate the underside of the penis, and (iii) releasing the band whereby the band contracts around the shaft of the penis, and the bump presses against and restricts the urethra.

A male wearing the device can urinate while wearing the device by consciously initiating voiding of his bladder without adjusting or removing the device, whereby (i) the bladder contracts, (ii) the bladder outlet relaxes, and (iii) the flow of urine within the urethra exerts a pressure sufficient to overcome the pressure exerted upon the urethra by the bump on the device so as to permit micturition.

The device, when equipped with removal loops, can be removed from operable engagement with a penis by (i) inserting at least one finger tip from a first hand into the first removal loop, and inserting at least one finger tip from a second hand into the second removal loop, (ii) manually stretching the elastic compression band so as to enlarge the lumen by pulling the loops away from one another, and (iii) sliding the manually stretched elastic compression band off the penis.

The device, when equipped with removal loops, can also be removed from operable engagement with a penis by (i) inserting at least a first and a second finger tip from a first hand into the first removal loop, and inserting at least a first and a second finger tip from a second hand into the second removal loop, (ii) manually radially stretching the elastic compression band so as to enlarge the lumen by both pulling the loops away from one another and expanding the first and second finger tips in each removal loop away from one another, and (iii) sliding the manually stretched elastic compression band off the penis.

An object of this invention is to provide a male incontinence control device that can be worn in comfort day and night, constructed of elastomeric material or compounds including, but not limited to, Silicone rubber, natural Rubber, Thermoplastic Elastomers (TPE), Thermoplastic Rubbers (TPR) and similar elastomer and elastomeric materials.

Another object of this invention is to provide a male incontinence control device that allows normal blood circulation to the penis while being worn for extended periods of time.

Another object of this invention is to provide a male incontinence control device that significantly impedes involuntary urinary flow.

Another object of this invention is to provide a male incontinence control device that typically requires no management or adjustment before, during, or after urination.

Another object of this invention is to provide a male incontinence control device that minimizes skin irritations.

Another object of this invention is to provide a male incontinence control device that is adjustable in tension by removal of material.

Another object of this invention is to provide a male incontinence control device that can be worn while sleeping.

Another object of this invention is to provide a male incontinence control device that does not require adjustment from a day's beginning to end, after the initial adjustment/fitting.

Another object of this invention is to provide a male incontinence control device that is easy to don and doff.

Another object of this invention is to provide a male incontinence control device that may employ an integrated protrusion disposed at the lower interior of the main sleeve body that can be modified in size or hardness by the use of inserts or caps to increase or decrease the height, length, width and/or hardness of said protrusion.

Another object of this invention is to provide a male incontinence control device constructed of a flexible body that allows urine to flow through the point of constriction, when urinary pressures within the urethra are increased, without prior adjustment or removal of the device.

Another object of this invention is to provide a male incontinence control device that additionally improves performance in impeding involuntary leakage when sitting.

Another object of this invention is to provide a male incontinence control device that may employ an integrated protrusion disposed at the lower interior of the main sleeve body which contains a harder insert molded core element to provide a firmer protrusion.

DETAILED DESCRIPTION OF A PREFERRED EMBODIMENT

Definitions

As utilized herein, including the claims, the phrase "essentially aligned", when used in reference to the position of the volumetric center of the bump relative to the minor axis of the lumen, means less than about 2 mm distance from the minor axis along a 90° straight-line.

As utilized herein, including the claims, the phrase "generally spherical object" means an object having no sharp edges or corners, such as a sphere, a torus, an ellipsoid, an egg-shaped object, a pear-shaped object, a 100-sided polyhedron, etc.

| Nomenclature Table | |
|---|---|
| Ref. No. | Name |
| 100 | Male Incontinence Control Device |
| 110 | Elastic Compression Band |
| | Elastic Cylindrical Annulus |
| | Sleeve |
| 110a | Top Portion of Elastic Compression Band |
| 110b | Bottom Portion of Elastic Compression Band |
| 110s | Side Portions of Elastic Compression Band |
| 119 | Lumen Through the Elastic Compression Band |
| | Void |
| 119α | Axial Directions of Lumen |
| 119α$_1$ | Forward Axial Direction of Lumen |
| 119α$_2$ | Rearward Axial Direction of Lumen |
| 119β | Radial Directions of Lumen |
| 119x | Length of Lumen |
| 120 | Bump |
| | Protrusion |
| 130 | Removal Appliances (Loops) |
| | Gripping Appendages |
| 131 | First Removal Appliance |
| 132 | Second Removal Appliance |
| 140 | Radial Wings |
| 141 | First Radial Wing |
| 142 | Second Radial Wing |
| 150 | Axial Wings |
| 151$_1$ | First Forward Axial Wing |
| 152$_1$ | Second Forward Axial Wing |
| 151$_2$ | First Rearward Axial Wing |
| 152$_2$ | Second Rearward Axial Wing |
| 200 | Insert |
| 300 | Post for Detachable Mounting of Bump |
| 410 | Inelastic Length of Band |
| 420 | Elastic Length of Band |
| 430 | Connection Mechanism |
| P | Penis |
| P$_1$ | Shaft of Penis |
| P$_2$ | Underside of Penis |
| S | Scrotum |
| U | Urethra |
| W | Wearer |

Construction

The male incontinence control device 100 is designed with comfort being one objective. It is constructed with a low modulus of elasticity elastomer material that allows the user to remain unaware of its presence throughout the day, when properly sized.

The male incontinence control device 100 is preferably configured and arranged not to completely impede urinary flow, but to greatly reduce involuntary urine flow while remaining comfortable to wear without inconvenience. In its preferred configuration and arrangement, persons wearing the device 100 may experience minor leakage for a variety of reasons throughout the day. Sudden increases in intravesical pressure may be generated when lifting a heavy weight, pressures from a full bladder, involuntary relaxation of the sphincter, or simply coughing or sneezing, in addition to urge incontinence.

The profile of the male incontinence control device 100 is modest in each dimension, which minimizes body contact and any tendency for movement. Comfort is directly related to the degree of constriction, which affects blood flow, and friction. Friction is created by contact pressures and movement between the device 100 and the surface of the skin.

Referring generally to FIGS. 1-5, according to the principles of the invention, the main body construction of the male incontinence control device 100 is a generally elastic cylindrical annulus, referred to herein as a sleeve or continuous loop elastic compression band 110, and an integrated protrusion, referred to herein as a bump 120, on the interior wall. The band 110 and bump 120 are preferably formed as a single-piece. Attached gripping appendages, referred to herein as removal appliances or removal loops 130, are preferably provided.

Figure 1:
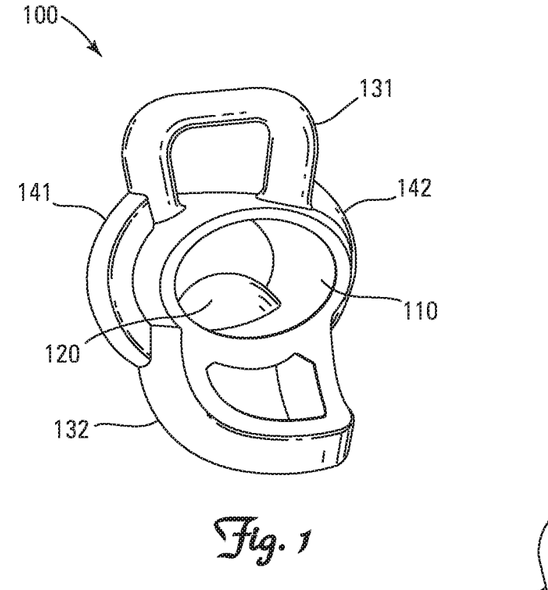
FIG. 1 is a perspective view of one embodiment of the invention.
Figure 2:
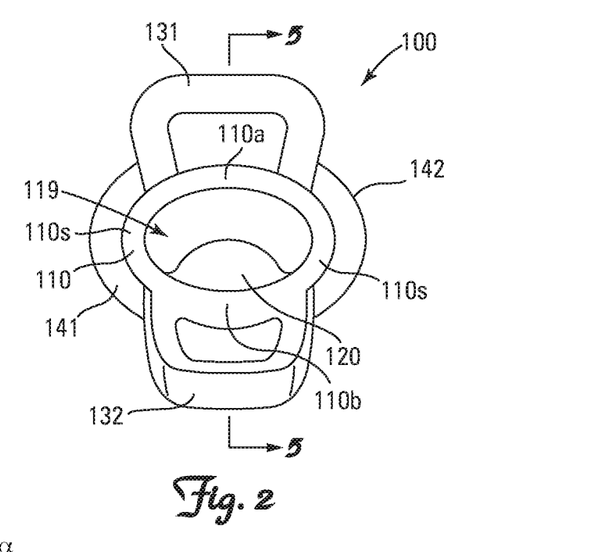
FIG. 2 is a front view of the invention depicted in FIG. 1.
Figure 3:
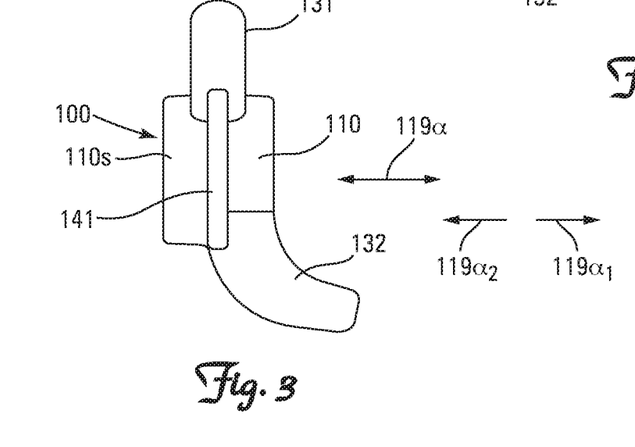
FIG. 3 is a side view of the invention depicted in FIG. 1.
Figure 4:
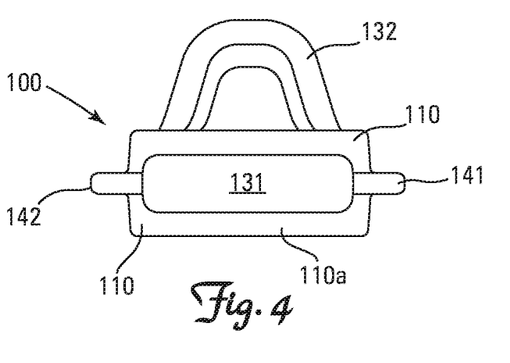
FIG. 4 is a top view of the invention depicted in FIG. 1.

Referring generally to FIGS. 1 and 2, the outer surface and the inner surface of the sleeve 110 defines the majority of the body of the sleeve 110. The inner face of the sleeve 110 bounds a cylindrical void, referred to herein as a lumen 119, which receives the penis P in the applied condition. The inner circumference of the sleeve 110 corresponds to, but is less than that of the flaccid penis P so as to securely encircle the flaccid penis P without inflicting penile ischemia.

An elastic compression band 110 having a thickness of 1 to 5 mm and defining a lumen 119 having an axial length of 1 to 2 cm is generally effective for providing a combination of comfort and superior performance.

The continuous loop elastic compression band 110 can be conveniently demarcated for purposes of describing the relative location of features and components on the continuous loop elastic compression band 110 as having a top portion 110$a$, a bottom portion 110$b$, and side portions 110$s$. The lumen 119 defines an axial direction 119$\alpha$ and radial directions 119$\beta$. The axial direction 119$\alpha$ has a forward axial direction 119$\alpha_1$ and a rearward axial direction 119$\alpha_2$. The lumen 119 has an axial length 119$x$.

The lumen 119 can have an elliptic cross-section with a major axis centered through the top 110$a$ and bottom 110$b$ portions of the elastic compression band 110 and a minor axis centered through the side portions 110$s$ of the elastic compression band 110.

The continuous loop elastic compression band 110 provides a relatively large cylindrical surface area in contact with the surface of the penis P relative to that of the small integrated protrusion 120 deposed at the lower 110$b$ interior of the main sleeve body 110 which concentrates upward pressure on the urethra U located on the underside $P_2$ of the penis P to impede urinary flow. This spreads constriction forces over a larger area around the perimeter of the penis P, relative to other configurations such as a cylindrical shaped (cross-section) loop, thereby allowing for normal blood flow and avoiding penile ischemia by minimizing constriction pressure. The distributed constriction force results in low pressures on the grouping of veins, arteries, and nerves commonly referred to as the neurovascular bundle, which ensures normal circulation and comfort.

The continuous cylindrical sleeve 110 is composed of a rubber, silicone or other elastomer commonly known to the trade. The sleeve 110 preferably has (i) a shore durometer of 5 A to 30 A, (ii) a low modulus of elasticity (i.e., a Young's Modulus of 5 to 30 psi and preferably 5 to 20 psi), and (iii) an ultimate elongation of at least 100%. A durometer of less than about 5 A tends to provide insufficient constriction force when used, while a durometer of greater than about 30 A tends to be excessively difficult to stretch when donning and doffing the device 100. Similarly a modulus of elasticity of less than about 5 psi tends to provide insufficient constriction force when used, while a modulus of elasticity of greater than about 30 psi tends to be excessively difficult to stretch when donning and doffing the device 100. Finally, an ultimate elongation of less than 100% tends to be excessively difficult to stretch a sufficient amount when donning and doffing the device 100.

Figure 5:
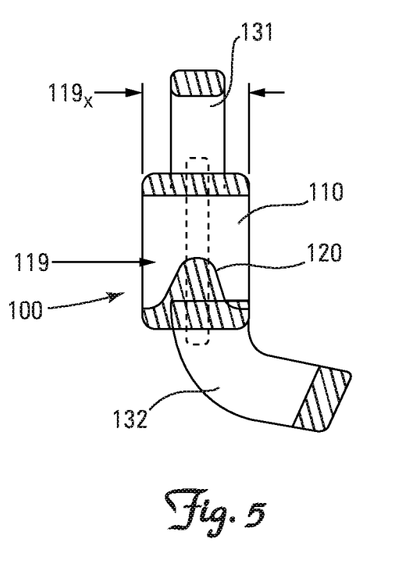
FIG. 5 is a cross-sectional view of the invention depicted in FIG. 2 taken along line 5-5.

Referring generally to FIGS. 1, 2 and 5, an integrated protrusion 120 is deposed on the inner wall of the continuous cylindrical sleeve 110 at the bottom 110$b$, extending radially inwardly and upward when in the applied condition for pressing against and constricting the urethra U of a wearer W.

A bump 120 which radially extends 5 to 15 mm into the lumen 119 is generally effective for providing a combination of comfort and superior performance.

In the preferred embodiment, the bump 120 has an uppermost convex surface, and is integrally attached to the lower 110$b$ interior of the inner wall of the sleeve 110. The bump 120 preferably projects radially inward 119$\beta$ directly towards the center of the lumen 199. Other embodiments may include, but are not limited to, protrusions composed of caps or inserts, which may not be an integral component to the sleeve 110 itself.

Referring generally to FIGS. 8-11, the bump 120 may be of solid elastomer material or may incorporate a variety of insert/snap-on components 200 of different size, shape and/or hardness (durometer) for insertion into a void within the bump 120 to increase hardness, adding to upward pressure on the urethra U. Alternatively, bumps 120 of different size, shape and/or hardness (durometer) may selectively attachable to the continuous cylindrical sleeve 110 via an inwardly projecting post 300 on the sleeve 110 to adjust upward pressure on the urethra U.

Referring generally to FIGS. 2 and 5, when the lumen 119 defined by the continuous loop elastic compression band 110 has an elliptic cross-section, the volumetric center of the bump 120 is preferably essentially aligned with the minor axis of the lumen 119.

Referring generally to FIGS. 1-5, the male incontinence control device 100 may have gripping appendages, referred to herein as removal appliances or removal loops 130 in the preferred embodiment, integrally attached to the continuous cylindrical sleeve 110. A first removal appliance 131 is deposed at the upper perimeter outer wall 110$a$ extending radially outward, and an opposed second removal appliance 132 is deposed at the lower perimeter outer wall 110$b$. The lower removal appliance 132 may be attached at a forward 119$\alpha_1$ angle to the main body 110 and a forward 119$\alpha_1$ angle when in the applied condition. This forward 119$\alpha_1$ bias from a horizontal or vertical axis, which is directed away from the body, can reduce contact with skin around the penis P.

The removal appliances 130 may be of any shape capable of allowing the continuous cylindrical sleeve 110 to be manipulated as necessary with ease and efficiency. Elderly men or those with impaired vision or dexterity should have little difficulty placing the device 100 into the proper position, particularly when the removal appliances 130 are formed as loops.

Referring generally to FIGS. 1-5, the removal appliances 130 are preferably configured and arranged for manual fingertip engagement to facilitate manual outward radial stretching of the elastic compression band 110. For ease of use, the removal appliances 130 are preferably diametrically opposed removal loops configured and arranged to accommodate passage of at least one fingertip and preferably two fingertips through each removal loop to facilitate manual outward radial stretching of the elastic compression band 110. When the lumen 119 defined by the continuous loop elastic compression band 110 has an elliptic cross-section, the removal appliances preferably extend radially outward from the elastic compression band in alignment with the minor axis of the lumen 119.

Referring generally to FIGS. 1, 3, 5 and 12, the removal appliance 130 closest to the bump 120 will typically contact and rub against the scrotum S during normal usage. In order to minimize any discomfort this removal appliances 130 can be angled axially forward $119\alpha_1$ from the elastic compression band 110. To further minimize any discomfort this scrotum-engaging removal appliances 130 preferably curves axially forward $119\alpha_1$ from the elastic compression band 110 at a radius of curvature of between about 1 to 2 cm, with the understanding that the curvature may be a compound curve with or without some linear segments which approximates a radius of curvature of between about 1 to 2 cm.

The gripping appendages 130 of other embodiments may be of another shape, size, material and position, lending to aesthetic or functional qualities.

Referring generally to FIGS. 1-4, the male incontinence control device 100 may include opposed trimmable appendages, referred to herein as radial wings 140 extending radially outward from the continuous loop elastic compression band 110.

The radial wings 140 preferably have an axial 119$a$ length of less than ½ that of the elastic compression band 110 so as to provide a limited area of increased radial thickness of elastic material to the side portions 110$s$ of the elastic compression band 110.

In a preferred embodiment, the opposed removable radial wings 140 project laterally (i.e., radially) from the side portions 110$s$ of the sleeve 110 outer wall a radial distance of between 2 and 10 mm when in the applied condition, with a first radial wing 141 projecting from a first side portion and a second radial wing 142 projecting from a second side portion. The radial wings 140 are preferably constructed of the same soft elastic material as the sleeve 110, sufficient in volume to increase sleeve 110 tension when in the applied condition and therefore, when removed or reduced, will decrease tension to adjust for varying user needs.

To adjust for proper tension and to ensure normal blood circulation when in the applied condition, the opposing radial wings 140 may be trimmed using common scissors to incrementally remove material.

Figure 6:
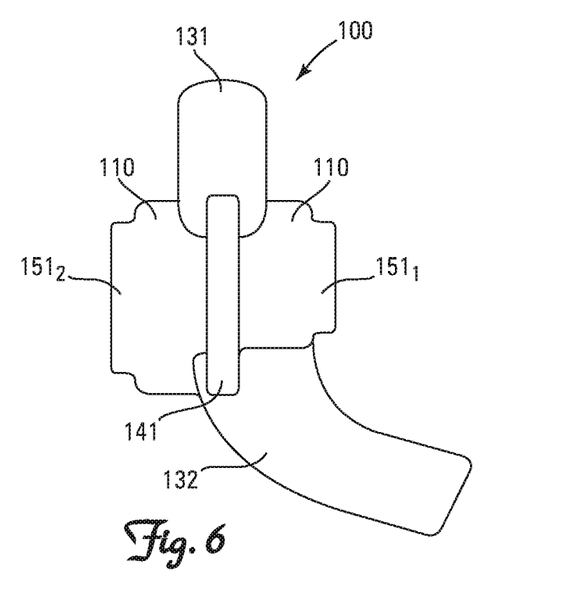
FIG. 6 is a side view of the invention depicted in FIG. 1 equipped with axial wings.
Figure 7:
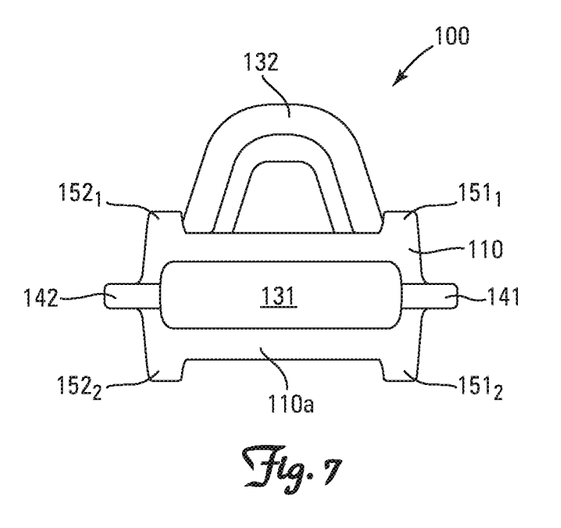
FIG. 7 is a top view of the invention depicted in FIG. 6.
Figure 8:
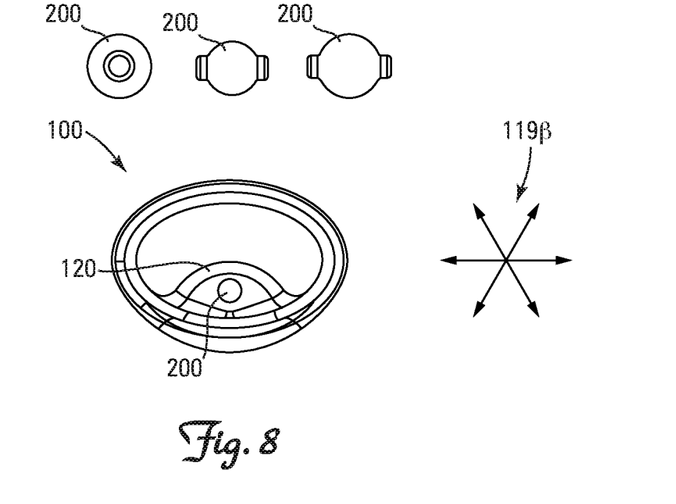
FIG. 8 is a front view of a second embodiment of the invention and multiple spherical objects configured and arranged for selective insertion into the bump.
Figure 9:
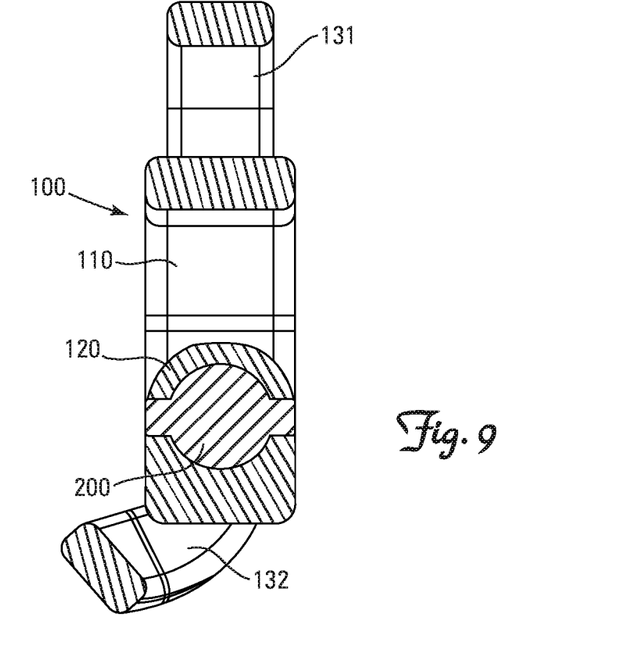
FIG. 9 is a cross-sectional view of a second embodiment of the invention equipped with a generally spherical object replaceably captured within the bump.
Figure 10:
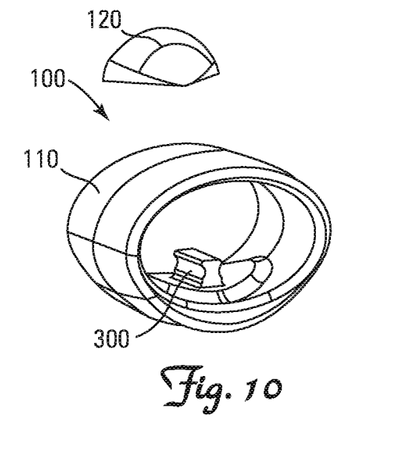
FIG. 10 is an exploded perspective view of a third embodiment of the invention having a detachable and replaceable bump.
Figure 11:
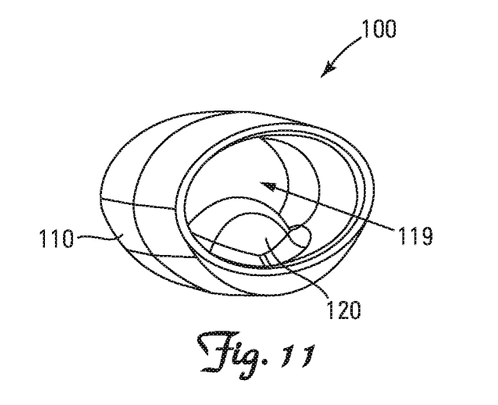
FIG. 11 is a perspective view of the third embodiment of the invention depicted in FIG. 10 with the bump attached to the band.
Figure 12:
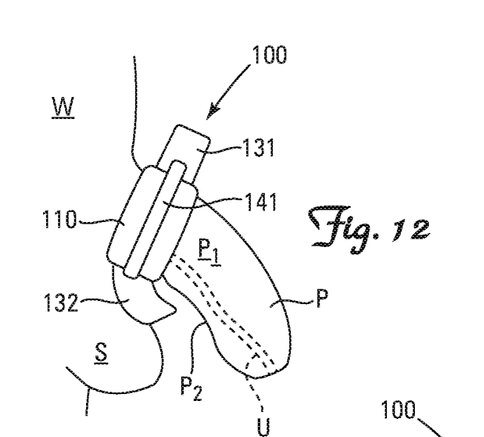
FIG. 12 is a side view of the invention depicted in FIGS. 1-5 worn by an individual.

Referring generally to FIGS. 6 and 7, the male incontinence control device 100 may, in addition to or instead of the radial wings 140, include forward $119\alpha_1$ and/or rearward $119\alpha_2$ extending pairs of laterally opposed trimmable appendages, referred to herein as axial wings 150 extending from the continuous loop elastic compression band 110.

The removable axial wings 150 project longitudinally (i.e., axially) forward $119\alpha_1$ and/or rearward $119\alpha_2$ from the side portions 110$s$ of the sleeve 110 an axial distance of between 2 and 10 mm when in the applied condition. A first forward axial wing 1511 projects from a first side portion 110$s$ and a second forward axial wing 1521 projects from a second side portion 110$s$. In similar fashion, a first rearward axial wing 1512 projects from a first side portion 110$s$ and a second rearward axial wing 1522 projects from a second side portion 110$s$. The axial wings 150, as with the radial wings 140 are preferably constructed of the same soft elastic material as the sleeve 110, sufficient in volume to increase sleeve 110 tension when in the applied condition and therefore, when removed or reduced, will decrease tension to adjust for varying user needs.

To adjust for proper tension and to ensure normal blood circulation when in the applied condition, the axial wings 150 may, as with the radial wings 140, be trimmed using common scissors to incrementally remove material.

Other embodiments may include removable features of another shape or size sufficient to modify functional qualities.

The male incontinence control device 100 (i.e., the continuous loop elastic compression band 110, bump 120, removal appliances 130 and radial wings 140) may be formed as a unitary molding of the elastomer material, employing injection, transfer, or compression molding processes.

Figure 13:
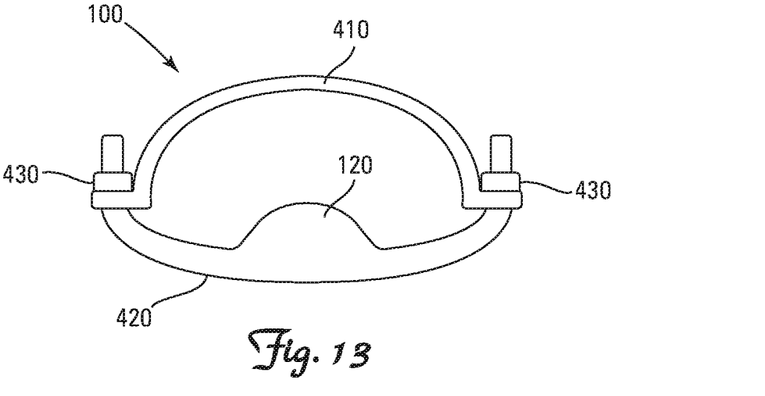
FIG. 13 is a front view of a fourth embodiment of the invention.

Other embodiments may incorporate rigid inelastic sections within the cylindrical annulus 110, which may be composed of, but not limited to, thermoplastics including ABS, polypropylene and nylon or thermosetting materials including phenolic and melamine, ceramics or hard elastomers, in addition to section(s) of soft elastic material. Referring generally to FIG. 13, one example of an embodiment incorporating a rigid inelastic section is a continuous loop band 110 formed from a rigid upper section body 410 and a flexible lower section 420 connected by a suitable connection mechanism 430. The ratio between the peripheral length of the rigid upper section body 410 and the peripheral length of the flexible lower section 420 can be varied.

Those skilled in the art will recognize that changes and modifications may be made in the described embodiments without departing from the nature and scope of the present invention. To the extent that such modifications and variations do not depart from the spirit of the invention, they are intended to be included within the scope thereof.

Method of Donning to Control Incontinence

The device 100 is operable for controlling male incontinence, by (i) manually radially stretching the continuous elastic compression band 110 so as to enlarge the lumen 119, (ii) inserting the penis P of a male W in need of incontinence control through the enlarged lumen 119 with the bump 120 on the device 100 positioned proximate the underside $P_2$ of the penis P, and (iii) releasing the band 110 whereby the band 110 contracts around the shaft $P_1$ of the penis P, and the bump 120 presses against and restricts the urethra U.

Expanding the sleeve 110 for application to the shaft $P_1$ of the penis P near the base can be achieved by insertion of the index finger and middle finger (not shown) of each hand (not shown) into the sleeve 110 center and pulling in opposite directions. The low modulus characteristic of the elastomer allows the unit 110 to be stretched sufficiently prior to positioning in the applied condition. The removal therefrom can be achieved by use of the respective gripping appendages 130, when stretched in opposite radial directions.

The proper unit size and/or tension for different users varies, which could be addressed by manufacturing different size devices 100. This invention partially addresses such sizing needs with its design. Users W requiring less tension can remove material from the radial ring (i.e., the radial wings 140) outside the main body 110. After the proper tension is established, no additional sizing or adjustments should be necessary.

Urinating while Wearing the Device

Removal or adjustment of the device 100 is not necessary prior to, during, or after urination, due to the flexible characteristics of the soft body construction.

A male W wearing the device 100 can urinate while wearing the device 100 by consciously initiating voiding of his bladder without adjusting or removing the device 100, whereby (i) the bladder contracts, (ii) the bladder outlet relaxes, and (iii) the flow of urine within the urethra exerts a pressure sufficient to overcome the pressure exerted upon the urethra by the bump 120 on the device 100 so as to permit micturition.

Overnight Use

When necessary or desired, the device 100 may be worn throughout the night. However, it is recommended that the device 100 be positioned forward from the base of the penis P to gain skin relief after daytime use positioned at or near the base. During daytime use, if positioned forward, performance would normally be degraded, but not so at night, due to reduced intravesical pressures when lying down.

Method of Doffing

The device 100, when equipped with removal loops 130, can be removed from operable engagement with a penis P by (i) inserting at least one finger tip from a first hand into a first removal loop 131, and inserting at least one finger tip from a second hand into the other removal loop 132, (ii) manually stretching the elastic compression band 110 so as to enlarge the lumen 119 by pulling the loops 130 away from one another, and (iii) sliding the manually stretched elastic compression band 110 off the penis P.

Alternatively, a wearer W can insert at least a first and a second finger tip from a first hand into the first removal loop 131, and inserting at least a first and a second finger tip from a second hand into the other removal loop 132, and then, in addition to manually stretching the elastic compression band 110 so as to enlarge the lumen 119 by pulling the loops 130 away from one another, expanding the first and second finger tips in each removal loop 130 away from one another.

We claim:

1. A male incontinence control device, comprising a continuous single-piece body including:
   (a) a loop of a stretchable elastic compression band defining a lumen, the stretchable elastic compression band configured and arranged to securely encircle a flaccid penis without inflicting penile ischemia, and
   (b) an inwardly projecting bump on the stretchable elastic compression band configured and arranged for pressing against and constricting an urethra of a wearer.

2. The male incontinence control device of claim 1 wherein the stretchable elastic compression band has a shore durometer of 5 A to 30 A.

3. The male incontinence control device of claim 2 wherein the stretchable elastic compression band has a thickness of 1 to 5 mm and the lumen has an axial length of 1 to 2 cm.

4. The male incontinence control device of claim 1 wherein the stretchable elastic compression band has a Young's Modulus of 5 to 30 psi.

5. The male incontinence control device of claim 1 wherein the stretchable elastic compression band has an ultimate elongation and the ultimate elongation of the stretchable elastic compression band is at least 100%.

6. The male incontinence control device of claim 1 wherein the bump radially extends 5 to 15 mm into the lumen.

7. The male incontinence control device of claim 6 wherein the stretchable elastic compression band and the elastic bump each have (i) shore durometers of 5 A to 30 A, (ii) Young's Modulus of 5 to 30 psi, and (iii) ultimate elongation of at least 100%.

8. The male incontinence control device of claim 1 further comprising two removal appliances extending radially outward from the stretchable elastic compression band, configured and arranged for manual fingertip engagement to facilitate manual outward radial stretching of the stretchable elastic compression band.

9. The male incontinence control device of claim 8 wherein the removal appliances are removal loops extending radially outward from the stretchable elastic compression band, configured and arranged to accommodate passage of at least one fingertip through each removal loop to facilitate manual outward radial stretching of the stretchable elastic compression band.

10. The male incontinence control device of claim 1 further comprising a generally spherical object having a durometer different from the bump replaceably captured within the bump.

11. The male incontinence control device of claim 1 wherein (i) the lumen has an elliptic cross-section with a major axis centered through a top and bottom portion of the stretchable elastic compression band and a minor axis centered through side portions of the stretchable elastic compression band, and (ii) the volumetric center of the bump is essentially aligned with the minor axis.

12. The male incontinence control device of claim 11 further comprising diametrically opposed first and second removal loops extending radially outward from the stretchable elastic compression band in alignment with the minor axis of the lumen, the removal loops configured and arranged to accommodate passage of at least one fingertip through each removal loop to facilitate manual outward radial stretching of the stretchable elastic compression band.

13. The male incontinence control device of claim 12 wherein the lumen defines a central axis projecting axially forward and axially backward and encircled by the stretchable elastic compression band, the second removal loop is closest to the bump, and the first removal loop projects both radially outward and axially forward from the stretchable elastic compression band.

14. The male incontinence control device of claim 13 wherein the second removal loop curves axially forward from the stretchable elastic compression band at a radius of curvature of between about 1 to 2 cm.

15. The male incontinence control device of claim 12 further comprising radial wings formed as a single-piece with the stretchable elastic compression band and extending radially outward from the side portions of the stretchable elastic compression band between the diametrically opposed removal loops, the radial wings having an axial length of less than ½ that of the stretchable elastic compression band so as to provide a limited area of increased radial thickness of stretchable elastic material to the side portions of the stretchable elastic compression band.

16. The male incontinence control device of claim 15 wherein the radial wings extend a radial distance of between 2 and 10 mm from the stretchable elastic compression band.

17. A method of removing a male incontinence control device in accordance with claim 12 from operable engagement with a penis, comprising the steps of:
   (a) inserting at least one finger tip from a first hand into the first removal loop, and inserting at least one finger tip from a second hand into the second removal loop,
   (b) manually stretching the stretchable elastic compression band so as to enlarge the lumen by pulling the removal loops away from one another, and
   (c) sliding the manually stretched stretchable elastic compression band off the penis.

18. A method of removing a male incontinence control device in accordance with claim 12 from operable engagement with a penis, comprising the steps of:
   (a) inserting at least a first and a second finger tip from a first hand into the first removal loop, and inserting at least a first and a second finger tip from a second hand into the second removal loop, (b) manually radially stretching the stretchable elastic compression band so as to enlarge the lumen by both pulling the removal loops away from one another and moving the first and second finger tips in each removal loop away from one another, and (c) sliding the manually stretched stretchable elastic compression band off the penis.

19. A method of controlling male incontinence, comprising the steps of:

(a) obtaining a male incontinence control device in accordance with claim 1, (b) manually radially stretching the continuous stretchable elastic compression band so as to enlarge the lumen, (c) inserting the penis of a male in need of incontinence control through the enlarged lumen with the bump on the stretchable elastic compression band positioned proximate an underside of the penis, and (d) releasing the stretchable elastic compression band whereby (i) the stretchable elastic compression band contracts around a shaft of the penis, and (ii) the bump presses against and restricts the urethra.

20. A method of urinating while wearing a male incontinence control device in accordance with claim 1, comprising the step of consciously initiating voiding of a bladder without adjusting or removing the device, whereby (i) the bladder contracts, (ii) the bladder outlet relaxes, and (iii) a flow of urine within the urethra exerts a pressure sufficient to overcome a pressure exerted upon the urethra by the bump on the stretchable elastic compression band so as to permit micturition.

* * * * *